United States Patent [19]

Takino et al.

[11] 4,046,893
[45] Sept. 6, 1977

[54] TRIOXOPTERIDINE DERIVATIVES SUITABLE AS MEDICAMENT

[75] Inventors: Masuichi Takino, Narashi; Teikichi Kurosaki; Munehiko Odaka, both of Osaka, all of Japan

[73] Assignee: Nippon Zoki Pharmaceutical Co., Ltd., Osaka, Japan

[21] Appl. No.: 650,749

[22] Filed: Jan. 20, 1976

Related U.S. Application Data

[63] Continuation-in-part of Ser. No. 396,810, Sept. 13, 1973, Pat. No. 3,946,012.

[30] Foreign Application Priority Data

Sept. 13, 1972 Japan .................................. 47-91907

[51] Int. Cl.² .......................................... A61K 31/505
[52] U.S. Cl. ..................................................... 424/251
[58] Field of Search .............................. 424/253, 251

*Primary Examiner*—Stanley J. Friedman
*Attorney, Agent, or Firm*—Birch, Stewart, Kolasch and Birch

[57] ABSTRACT

Trioxopteridine derivatives of the formula

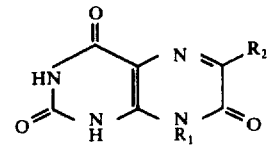

, wherein $R_1$ is a normal alkyl group having 0 to 6 hydroxyl groups and $R_2$ is hydrogen or a normal lower alkyl group having 0 to 5 hydroxyl groups, are prepared by catalytically hydrogenating a 6-substituted-5-nitro-2,4-dioxopyrimidine to give a 6-substituted-5-amino-2,4-dioxopyrimidine, and then reacting the latter compound with a compound of the formula $R_2$—A—$COOR_3$, wherein $R_3$ is hydrogen, lower alkyl, an alkali metal or an alkaline earth metal and A is carbonyl or a group of the formula

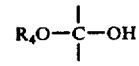

wherein $R_4$ is lower alkyl. The resulting trioxopteridine derivatives have analgesic and antiphlogistic properties and are therefore useful as pharmaceutical medicaments.

3 Claims, No Drawings

TRIOXOPTERIDINE DERIVATIVES SUITABLE AS MEDICAMENT

This application is a continuation-in-part of copending application Ser. No. 396,810, filed on Sept. 13, 1973, now U.S. Pat. No. 3,946,012.

BACKGROUND OF THE INVENTION

The present invention relates to novel trioxopteridine derivatives and to processes for producing such compounds. More particularly, the invention relates to novel compounds having the following general formula:

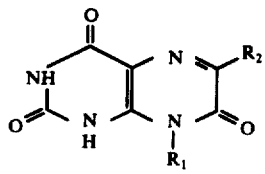
(IV)

wherein $R_1$ is a normal (straight chain) alkyl group having 0 to 6 hydroxyl groups, and $R_2$ is a hydrogen atom or a normal lower alkyl group having 0 to 5 hydroxyl groups.

The pharmaceutical industry is constantly striving to find and develop new compounds having various useful properties. In particular, such compounds must be safe and effective and without side effects. The present invention provides novel compounds having useful pharmaceutical properties.

One of the objects of the present invention is to provide novel trioxopteridine derivatives.

Another object of the invention is to provide an effective method for producing said compounds.

A further object of the invention is to provide novel compounds which are useful in combatting rheumatoid arthritis, arthralgia, frozen shoulders, chronic arthritis and like ailments.

These and other objects and advantages of the present invention will become apparent to those skilled in the art from a consideration of the following specification and claims.

SUMMARY OF THE INVENTION

In accordance with the present invention, the novel trioxopteridine derivatives (IV) are prepared by catalytically hydrogenating a 6-substituted-5-nitro-2,4-dioxopyrimidine of the formula:

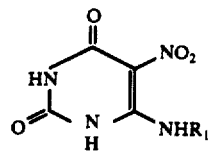
(I)

to give a 6-substituted-5-amino-2,4-dioxopyrimidine having the formula:

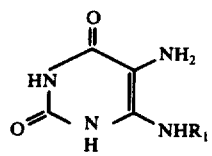
(II)

and then reacting said 6-substituted-5-amino-2,4-dioxopyrimidine with a compound of the formula:

$$R_2-A-COOR_3 \qquad (III)$$

wherein $R_3$ is a hydrogen atom, a straight- or branched-chain lower alkyl group, an alkali metal atom or an alkaline earth metal atom. A represents a carbonyl group or a group of the formula:

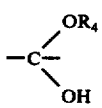

wherein $R_4$ is a lower alkyl group. The term "lower alkyl" in the present application refers to alkyl groups having from 1 to 5 carbon atoms.

Hence, the reaction sequence employed in the present invention may be shown as follows (where I-a and II-a are the tautomers of I and II, respectively):

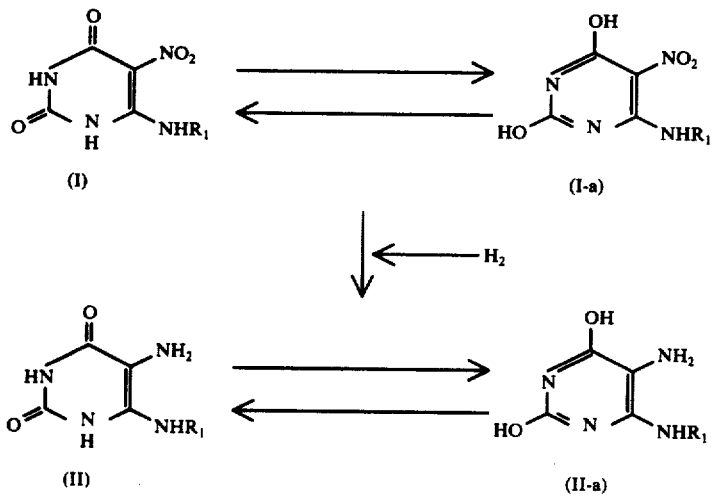

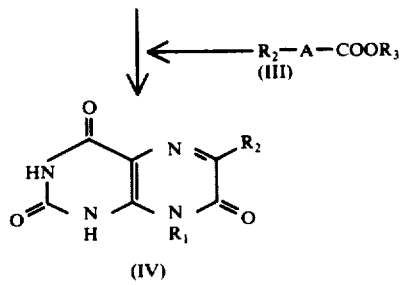

(IV)

More specifically, $R_1$, $R_2$, $R_3$ and $R_4$ in the above formulae represent, for example, the following groups.

$R_1$ may be methyl, ethyl, propyl, butyl, pentyl, hexyl, heptyl, hydroxymethyl, 2-hydroxyethyl, 2,3-dihydroxypropyl, 3,4-dihydroxybutyl, 2,3-dihydroxybutyl, 2,3,4-trihydroxybutyl, 2,3,4,5-tetrahydroxypentyl, 2,3,4,5,6-pentahydroxyhexyl, 2,3,4,5,6,7-hexahydroxyheptyl and other straight chain alkyl groups of 1 to 7 carbon atoms. Some of these groups contain asymmetric atoms or optical isomers, however, their isomers and mixtures thereof may be equally used effectively in the present invention.

$R_2$ is hydrogen or methyl, ethyl, propyl, butyl, hydroxymethyl, dihydroxyethyl, 1-hydroxyethyl, 1,2-dihydroxypropyl, trihydroxypropyl, tetrahydroxybutyl, pentahydroxypentyl and other straight chain lower alkyl groups having 0 to 5 hydroxyl groups. Some of these groups include optical isomers, however, such isomers and mixtures thereof are equally used in this invention.

$R_3$ represents, for example, methyl, ethyl, propyl, isopropyl, butyl, isobutyl and other straight- or branched-chain lower alkyl groups; sodium, potassium and other alkali metal atoms; and calcium, barium and other alkaline earth metal atoms.

$R_4$ is a straight or branched-chain lower alkyl such as methyl, ethyl, propyl or butyl.

Instead of using the compounds of formula (I) and formula (II), it is quite suitable and advantageous to use the tautomers represented by formula (I-a) and formula (II-a), respectively, in the reactions in the present invention. It is readily apparent that the quantity proportion of the mixture of tautomers to be employed depends on the specific reaction conditions, for example, the pH value of the solvent used in the reaction process, etc.

The hydrogenation of compound (I) is generally carried out under normal or increased pressure in the presence of a hydrogenation catalyst such as palladium, platinum oxide, Raney nickel or Raney cobalt. Water and/or an organic solvent, e.g., an alkanol, can be used in the reaction, and the reaction proceeds completely at room temperature even when water is employed.

The acid addition salts of compound (II) that are produced by the reaction of compound (I) with the inorganic or organic acid are quite stable. The compound (II) produced in the hydrogenation reaction sometimes includes some unstable products mixed therewith, however, even if only the catalyst is filtered therefrom, the solution can be reacted directly with compound (III) without separating the unstable products from the solution. It is desirable to carry out the filtration of the catalyst in an inert gas such as nitrogen, for example, under the pressure of nitrogen gas. In reacting compound (II) with compound (III), a liquid controller, for example, a weakly acidic alkali metal salt such as sodium acetate or potassium acetate, or ammonia is advantageously used for accelerating the velocity of the reaction. When a slightly unstable material such as 5-amino-2,4-dioxo-6-D-ribitylaminopyrimidine is involved in the reaction, the addition of an antioxidant such as an alkali metal salt, e.g., potassium disulfite, to the reaction mixture affords good results in the reaction.

The reaction is preferably conducted at a temperature of from about 0° to 100° C., and it is advantageous to start the reaction at a lower temperature and then to raise the temperature of reaction by heating during the course of the reaction process. In this way, the reaction proceeds selectively without destroying the configuration of the substituted radicals $R_1$ and $R_2$ because of the comparatively lower reaction temperature used at the beginning of the reaction.

Compound (IV) may be easily crystallized by methods well known in the art, such as concentration of the reaction solution under reduced pressure, or by the addition of crystallizing solvents to the reaction solution, and then purified by means of magnesium silicate column chromatography or anion exchange resin chromatography.

The novel compound (IV) of the present invention possesses analgesic and antiphlogistic activity. Accordingly, this compound is particularly useful as a remedy for rheumatoid arthritis, arthralgia, frozen shoulders, chronic arthritis and like disorders.

The trioxopteridine derivatives of the present invention can be readily formulated into a pharmaceutical composition by means well known in the art. For example, unit dosages of the compound may be mixed with conventional pharmaceutically acceptable, inert diluents, carriers or adjuvants. In this manner the compounds can be formulated as a tablet, capsule, syrup, elixir or injectable solution, as desired. For instance, an excipient such as the sugar lactose may be used with the trioxopteridine derivative in sufficient quantity to form a capsule or to form a powder which can be added to an aqueous solution to form a syrup.

EXAMPLES OF THE INVENTION

The following Examples are given merely as illustrative of the present invention and are not to be considered as limiting.

EXAMPLE 1

4.0 g of 6-L-arabitylamino-5-nitro-2,4-dioxopyrimidine dissolved in 150 ml of water is hydrogenated in the presence of a palladium active-carbon catalyst at room temperature. After adding 30 ml of 1N hydrochloric acid thereto, an aqueous solution of 5-amino-6-L-arabitylamino-2,4-dioxopyrimidine is obtained by the filtration of said catalyst from the resulting solution in a nitrogen atmosphere. Without isolation of the reaction product, the obtained solution is heated together with 2.0 g of ethyl pyruvate and 4.4 g of sodium acetate at 80° C. for 20 minutes. After filtering out the crystals produced by cooling the solution in an ice bath, the crystals are dissolved in 100 ml of water at a pH of 9.0 by means of heating. Then, this solution is adjusted to a pH of 1.0 with 6N hydrochloric acid to obtain a crystalline product by filtration. By crystallization from 300 ml of water, 2.8 g of dried pale yellow needle crystals of 8-L-arabityl-6-methyl-2,4,7-trioxopteridine is obtained.

Yield: 65.0%

M.P.: 289.0° - 290.5° C (with decomposition)

Analysis — calculated for $C_{12}H_{16}N_4O_7$: Theory: C, 43.90; H, 4.91; N, 17.07%. Found: C, 44.29; H, 4.91; N, 16.90%.

Specific rotary power:

$[\alpha]_D^{20}$ + 12.60 (C=0.230, in pH 8.0 buffer solution of phosphoric acid)

pKa value:

3.60 ± 0.02, 12.93 ± 0.02

EXAMPLE 2

1.0 g of 5-nitro-2,4-dioxo-6-D-xylytyl-aminopyrimidine is dissolved in 50 ml of water and adjusted to a pH of 10 with 7.5N ammonia water. The resulting compound in this solution is reduced in a hydrogen atmosphere in the presence of palladium catalyst. After the reaction is completed, 15 ml of 1N hydrochloric acid is added to the resultant solution. Then, the catalyst in the solution is filtered off under pressurized nitrogen gas to obtain 5-amino-2,4-dioxo-6-D-xylytylaminopyrimidine and to this filtrate is added 0.75 g of ethylglyoxylate hemi-acetal. After adjustment to a pH of 5 with 2.2 g of sodium acetate, the precipitate is obtained by filtration. The precipitate is dissolved in 6 ml of 1N aqueous sodium hydrogen carbonate. The solution is concentrated to dryness under reduced pressure and is then dissolved in 3 ml of water by means of heating. The solution is kept under cold storage and is filtered to obtain a crystalline material. After the crystalline material is recrystallized from 90% ethanol (pH 1.5) and then from water, 0.46 g of crystals of 2,4,7-trioxo-8-D-xylytylpteridine is obtained.

Yield: 44.8%

M.P.: 250.0° - 251.5° C

Analysis — calculated for $C_{11}H_{14}N_4O_7$: Theory: C, 42.04; H, 4.49; N, 17.83%. Found: C, 41.93; H, 4.40; N, 17.42%.

Specific rotary power:

$[\alpha]_D^{20}$ + 16.40 (C=0.235, in pH 8.0 buffer solution of phosphoric acid)

$[\alpha]_D^{20}$ − 1.82 (C=0.220, 0.1N-HCl)

pKa value:

3.18 ± 0.02, 12.45 ± 0.01

EXAMPLE 3

1.65 g of 6-D-lyxityl-5-nitro-2,4-dioxopyrimidine dissolved in 150 ml of water is reduced in the presence of palladium catalyst to obtain 5-amino-6-D-lyxitylamino-2,4-dioxypyrimidine and is condensed with 0.8 g ethyl pyruvate under weak acidity. After heating with stirring for 1½ hours, the solution is concentrated to 50 ml and adjusted to a pH of 1.0. 200 ml of ethanol is added to the filtrate of this solution, and the solution is cooled. The resulting precipitate is recrystallized from water, and 0.85 g of pale yellow needle crystals of 8-D-lyxityl-6-methyl-2,4,7-trioxopteridine is obtained.

Yield: 48.0%

M.P.: 267.0° - 268.5° C (with decomposition)

Analysis — calculated for $C_{12}H_{16}N_4O_7$: Theory: C, 43.90; H, 4.91; N, 17.07%. Found: C, 44.01; H, 4.89; N, 16.97%.

Optical rotation:

$[\alpha]_D^{20}$ − 12.99° (C=0.300, in pH 8.0 buffer solution of phosphoric acid)

$[\alpha]_D^{20}$ − 4.23° (C=0.260, 0.1N-HCl)

pKa value:

3.76 ± 0.01, 13.01 ± 0.02

EXAMPLE 4

5-nitro-2,4-dioxo-6-$\beta$-hydroxyethylaminopyrimidine is hydrogenated in the presence of Raney nickel, and the reaction product is purified to obtain 5-amino-2,4-dioxo-6-$\beta$-hydroxyethylaminopyrimidine hydrochloride. 2 g of the obtained compound and 300 mg of potassium disulfite are dissolved in 80 ml of water and to this solution is added 2 g of α-keto-D-calcium gluconate. Then the mixture is heated under reflux in a nitrogen atmosphere for 1 hour. After cooling, the filtrate is concentrated to 25 ml of solution. Thereafter, the solution is purified by means of magnesium silicate chromatography and strong base ion-exchange chromatography to obtain 1.0 g of 6-(D-arabo)-tetrahydroxybutyl-8-$\beta$-hydroxyethyl-2,4,7-trioxopteridine.

Yield: 32.4%

M.P.: 184° - 185° C (with decomposition)

Analysis — calculated for $C_{12}H_{16}N_4O_8$: Theory: C, 41.86; H, 4.68; N, 16.28%. Found: C, 41.51; H, 4.39; N, 16.33%.

Optical rotation:

$[\alpha]_D^{20}$ − 40.8 (C=0.270, in pH 8.0 buffer solution of phosphoric acid)

$[\alpha]_D^{20}$ − 47.7 (C=0.130, 0.1N-HCl)

pKa value:

3.25 ± 0.05, 12.80 ± 0.02

EXAMPLE 5

2 g of 5-nitro-2,4-dioxo-6-D-ribitylaminopyrimidine dissolved in 160 ml of water is reduced in the presence of palladium catalyst. 200 ml of filtrate is obtained by removal of the catalyst after the addition of hydrochloric acid thereto. To this solution is added 1.0 g of potassium disulfite and 5 g of α-keto-L-barium erythronate. The pH of the solution is then adjusted to pH 7.0 using sodium acetate . (3 hydrate). After refluxing in a nitrogen atmosphere for 2.5 hours, the insoluble product in the reaction solution is filtered out. The filtrate is adjusted to a pH of 1.5 and is purified by means of active carbon chromatography (extracted with 5% of pyridine solution) and magnesium silicate chromatography to obtain 0.72 g of 6-L-dihydroxyethyl-2,4,7-trioxo-8-D-ribityl pteridine.

Yield: 29.2%

M.P.: 136° - 139° C (with decomposition)

Analysis — calculated for $C_{13}H_{18}N_4O_9$: Theory: C, 41.71; H, 4.85; N, 14.97%. Found: C, 42.20; H, 4.59; N, 14.61%.

Optical rotation:

$[\alpha]_{320}^{22}$ − 5.72° × $10^4$ (C=3.86 × $10^{-3}$, pH 8.0 buffer solution of phosphoric acid)

$[\alpha]_{320}^{22}$ + 4.41° × $10^4$ (C=3.86 × $10^{-3}$, 0.1N-HCl)

pKa value:

3.36 ± 0.03, 12.44 ± 0.02

The following clinical results have been observed by the present inventors with the claimed compound:

(1) Analgesic effect on rheumatoid arthritis.

Samples containing 3 μg of pteridine A or pteridine B were subcutaneously injected into patients at intervals of 2 days. The results are shown in the following Table.

|  | Number of Patients (cases) | Number of Dosages (times) | Effect | | | |
|---|---|---|---|---|---|---|
|  |  |  | +++ | ++ | + | − |
| Pteridine A* | 24 | 22 | 10 | 9 | 4 | 1 |
|  |  | % | 41.7 | 37.5 | 16.6 | 4.2 |
| Pteridine B** | 25 | 22 | 1 | 4 | 12 | 8 |
|  |  | % | 4.0 | 16.0 | 48.0 | 32.0 |

*Pteridine A is the claimed compound, 6-dihydroxyethyl-2,4,7-trioxo-8-D-ribitylpteridine
**Pteridine B is 8-D-ribityl-6-methyl-2,4,7-trioxopteridine, a prior art compound (2) Antiphlogistic effect on rheumatoid arthritis Of 25 patients, 7 (1 man, 6 women) showed pain and swelling in one or more joints, despite the disappearance of most of the swelling due to treatment with the conventional drugs such as bethamethason (Schering), azapropazone (Siegfried) and indomethacin (Merck Sharp & Dohme). When the 7 patients were subcutaneously injected with Pteridine A (1 or 2 ampoules), 5 of them felt warm in the swollen joints within 10 minutes after the injection, and this warmth could be felt from the outside. The order of degree of this action of the Pteridine A was found to have almost the same degree as the analgesic effect shown hereinabove. That is, the warmer the joints became after the injection, the stronger was the analgesic effect. The remaining 20 patients did not feel the warmth in the joints which had pain and deformities only. Finally, for the study of the antiphlogistic effect, we selected 5 (1 man and 4 women) of the above 7 patients, because they had pain and fairly pronounced or pronounced swelling in one or more joints which resisted a long-term use of the above conventional drugs. The progress of the ailment, especially the swelling after the treatment with Pteridine A was as follows:

Case 1. A 56-year old woman had pain and swelling first in the right finger joints, and then the left knee and toe joints at the age of 52. At that time erythrocite sedimentation rate (Westergren) was normal. CRP was ++. Since then she was treated with indomethacin for about 4 years, but the ailment only partially improved. On her first visit to our clinic, erythrocyte sedimentation rate was 17mm in one hour (Westergren), CRP was negative. The right and left finger joints had fairly marked deformities: the left knee and the joints, especially the latter, had pain and swelling. She was injected with one ampoule of Pteridine A. Soon after the injection she felt slightly warm in the swollen joint, and the pain slightly improved. She was treated therewith (one ampoule daily) for two months. The ailment fairly improved. She was further treated therewith (one ampoule daily) for the following two months. She was able to put on her shoes and to walk without any pain.

Case 2. A 43-year old woman had pain in the sole of the left foot and then successively pain and swelling in all the finger and toe joints at the age of 27. The joints were only temporarily improved by corticosteroid. Only during the period of pregnancy at the age of 34 were they greatly improved, but soon after the parturition pain and swelling returned to the former diseased state. On her first visit to our clinic erythrocyte sedimentation rate was 17mm in one hour. ASLO was 166; CRP was +. She had pain and swelling in the left hand and finger joints and the right toe joints. She was injected with two ampoules of Pteridine A. Five minutes or so later she felt fairly warm in the swollen joints and the pain slightly improved. She was treated with Pteridine A (one ampoule daily) for two months. The ailment fairly improved. She continued to be treated therewith. About 20 days thereafter she was able to walk without limping, to put her shoes on without difficulty and to sit down, Japanese style, fourteen minutes for the first time.

Case 3. A 63-year old woman had 38° C. fever and a slight pain in the right and left knee joints at the age of 53. As the fever went down, she had pain in almost all of the joints, but swelling appeared only in the right and left knee joints. Most of the swelling disappeared completely due to corticosteroid except in the knee joints. In November at the age of 62 she had hydrarthrosis in the diseased knee joints. The swelling and hydrarthrosis of the right knee joint were removed by 2 months' treatment with a weekly puncture and an injection of corticosteroid, whereas that of the left joint resisted these treatments for 7 months. On the first day of our examination erythrocyte sedimentation rate was 38mm in one hour. CRP was +. ASLO was 125 units. The left knee joints showed swelling and fluctuation. She was injected with two ampoules of Pteridine A. Soon after the injection she felt slightly warm in the swollen joint, but the pain did not improve. She was treated with this drug (two ampoules daily) for a month and a half following the last puncture. The hydrarthrosis did not appear even after 4 months.

Case 4. A 40-year old woman had pain and swelling in the joints of the right hand at the age of 13. One year later, the symptoms also appeared in the left hand. She was treated by physical therapy. The symptoms disappeared while she was not aware of it. At the age of 23, she had pain and swelling in the joints of the left foot, the right knee, the right and left fingers and the toes. Since then the ailment gradually developed into the typical rheumatoid arthritis. She was treated with corticosteroid. Most of the swelling disappeared except for the hand and finger joints. For 3 years before our examination she had been treated with indomethacin. When she took one tablet of the drug (25 mg) before going to bed, and she was able to do her household duties in the morning. But, she was tormented with an upset stomach and dizziness. On the day of our first examination erythrocyte sedimentation rate was 33 mm in one hour. ASLO was 250 units; CRP was negative. Her hands showed the characteristic deformities and ulnar deviation of the fingers and pronounced swelling in spite of the above drug. She was injected with one ampoule of Pteridine A. In five minutes or so she felt very warm in the swollen joints and the pain fairly improved, so we continued to treat her with Pteridine A (one ampoule daily). Four days after the daily injection wrinkles appeared on the surface of the swelling. About 20 days after the treatment the swelling disappeared completely, but slight pain occurred, especially before bad weather set in. She is now being treated therewith.

Case 5. A 24-year old man had pain first in the right shoulder and foot joint for about one year before coming to us. Four months later he had pain successively in the sole of the right foot, the right ankle, the right and left hand and finger joints and finally in both the shoulders. He was treated with betamethason (1.0 mg to 3.0 mg daily) for 7 months. Most of the swelling disappeared. But, the pain and pronounced swelling in the right and the left hand and fingers, especially in the former, resisted the drug. On the day of our first examination erythrocyte sedimentation rate was 118mm in one hour. ASLO was 166 units; CRP was +++. He was injected with one ampoule of Pteridine A. Soon after the injection he felt fairly warm in the swollen joints and the pain slightly improved. After the dosage of the corticosteroid was decreased to 0.75 mg, he was treated with Pteridine A for the following 20 days, and the swelling and the pain greatly improved. He is now being treated therewith.

It is clear from these data and clinical studies that Pteridine A and B differ in their degree of effectiveness and, in fact, that Pteridine A is significantly more effective than Pteridine B. The mechanism of action of these pteridines upon the diseased joints has not as yet been clarified. However, it has been found that the swollen joints became warm soon after the injection of Pteridine A in five of the seven patients who had pain and swelling. This observation probably indicates that the Pteridine A dilates the blood vessels of the diseased joints. Furthermore, it has been noted that the analgesic and antiphlogistic effect of Pteridine A is strong, even dramatic in some cases, despite thrir small dosage (microgram units) in contrast to that (milligram units) of other antirheumatic drugs such as the corticosteroids, azapropazone and indomethacin.

Advantageously, the compound of the invention, Pteridine A, is administered in dosages of from 1 micrograms to 50 micrograms per day, in its utility as an analgesic and antiphlogistic agent as discussed herein.

The invention being thus described, it will be obvious that the same may be varied in many ways. Such variations are not to be regarded as a depature from the spirit and scope of the invention, and all such modifications are intended to be included within the scope of the following claims.

We claim:

1. An analgesic and antiphlogistic pharmaceutical composition comprising an effective analgesic and antiphlogistic amount of the compound 6-dihydroxyethyl-2,4,7-trioxo-8-D-ribitylpteridine and a pharmaceutically acceptable, inert diluent, carrier or adjuvant.

2. The pharmaceutical composition of claim 1, wherein said composition contains from 1 to 50 micrograms of said compound.

3. An analgesic and antiphlogistic pharmaceutical composition comprising an effective analgesic and antiphlogistic amount of the compound 6-dihydroxyethyl-2,4,7-trioxo-8-ribitylpteridine and a sugar lactose carrier.

* * * * *